United States Patent [19]

Fine et al.

[11] 4,119,402

[45] Oct. 10, 1978

[54] METHOD TO MEASURE IN VIVO N-NITROSO COMPOUNDS

[75] Inventors: David H. Fine, Framingham; Ronald D. Ross, Jr., Waltham; David P. Rounbehler, Concord, all of Mass.

[73] Assignee: Thermo Electron Corporation, Waltham, Mass.

[21] Appl. No.: 722,316

[22] Filed: Sep. 10, 1976

[51] Int. Cl.$^2$ .................... A61K 29/00; G01N 31/06; G01N 31/08; G01N 33/16
[52] U.S. Cl. .................................... 23/230 B; 424/9
[58] Field of Search ........................ 424/9; 23/230 B

[56] References Cited

U.S. PATENT DOCUMENTS

| 3,649,199 | 3/1972 | Littlejohn | 23/230 B |
| 3,877,873 | 4/1975 | Winitz | 23/230 B |
| 3,973,910 | 8/1976 | Fine | 23/230 RX |

OTHER PUBLICATIONS

Immuno-histochemical study of brain specific S-100 protein in exp. brain tumors.; Stravrou et al, Biological Abstracts Jan. 1, 1975, #3408.
Morphological studies of rat brain tumor induced by N-nitromethylurea, J. Neurosurgery vol. 34, Iss 3, 1971, p. 335–340. (Abstract only).
The preservation of meats and meat products: Its influence on nutritive and gustatory value and effects on human health, Hofmann Ba 74:17321.
Effect of fish-smoking technology in the Nitrosamine level in smoked fish; Vopr Onkol (Leningr) Goreliva et al., 1076.
The determination of total nonvolatile nitrosamines in microgram amts., Walters et al.; 1974.
Du Plessis et al.; Nitrosamine analysis part 1: The estimation of low molecular weight nitrosamines, 1972.
In vivo and in vitro exp. on the formation of N-nitroso compounds from amines/amides and nitrate/nitrite. Sander et al.

*Primary Examiner*—Morris O. Wolk
*Assistant Examiner*—Michael S. Marcus
*Attorney, Agent, or Firm*—James L. Neal

[57] ABSTRACT

A method by which in vivo N-nitroso compounds are detected. The N-nitroso compounds appear in the metabolic system or are formed therein from one or more precursors. The metabolic reactions are terminated instantly at a predetermined point in time, as by freezing in a liquidied gas, and the frozen sample is analyzed for the presence of N-nitroso compounds.

11 Claims, No Drawings

METHOD TO MEASURE IN VIVO N-NITROSO COMPOUNDS

BACKGROUND OF THE INVENTION

There exists a substantial body of evidence relating cancer in man to his exposure to N-nitroso compounds. Extensive laboratory tests on various species of animals strongly suggests N-nitroso compound exposure is casually related to cancer in animals.

This evidence includes the following:

Of the nearly one hundred N-nitroso compounds that have been tested, approximately eighty percent were active carcinogens for several animal species.

Carcinogenic nitrosamines have specific organotrophic effects, irrespective of their roots of administration.

Many N-nitroso compounds selectively produce cancer at various sites, such as the lung, stomach, liver and nasal cavity, in many animal species.

Biochemical activation of nitrosamines such as dimethylnitrosamine (DMN) to activate proximate carcinogens has been shown to be similar in both humans and rodents.

Repeated administration of low doses of N-nitroso compounds appears to be more effective in inducing cancers in rodents than administration of a single high dose.

In addition, it is known that N-nitroso compounds can be easily synthesized in foods and in vivo from common and naturally occuring precursors. Therefore, in investigating a connection between cancer in man and his exposure to N-nitroso compounds, it is important to have information on both the content of preformed N-nitroso compounds in the environment and in food and the possible formation of these compounds in vivo. Unfortunately more knowledge is needed relating to how man's exposure to preformed N-nitroso compounds compared to the in vivo formation from various precursors. That these compounds chemically react and change form within the body has been a major problem to obtaining this information. N-nitroso compounds formed from precursors appear to be present in the body for a relatively brief period of time.

Accordingly, it is an objective of the present invention to provide a method for directly measuring in vivo N-nitroso compounds.

It is a further objective of the present invention to provide a method of measurement which is simple and inexpensive, thereby facilitating routine evaluation of thousands of compounds and foodstuffs.

It is a further objective of the present invention to provide a method of measurement that is sensitive to all N-nitroso compounds.

It is a further objective of the present invention to provide a method for measurement that will work with real, complex mixtures, such as foodstuffs where the precursors are present at true environmental levels.

It is still a further objective of the present invention to provide a method of measurement which is unambiguous, with little inherent possibility for false results.

SUMMARY OF THE INVENTION

The method of the present invention involves a substance to be tested in a living biological system, such as the digestive system of a living test animal. The substance is allowed to react chemically in the animal's metabolic system for a predetermined period of time. At the end of this period, the reaction is terminated instantly and the N-nitroso compounds in the entire animal are measured and may be identified. In measuring N-nitroso compounds in animals raised under uniform controlled laboratory conditions, information is obtained as to the N-nitroso content verses time by introducing like samples into a number of animals and terminating the chemical reactions after different amounts of time. Preferably chemical reaction is terminated by immersing the animal into a very cold liquid which freezes the animal substantially instantly. Thereafter the animal is reduced to a fine frozen powder and N-nitroso compounds in the frozen powder are measured.

DETAILED DESCRIPTION OF THE INVENTION

The method of the present inventin may be initiated by introducing a sample of the substance to be tested into a living biological system, such as the digestive system of a living test animal. The substance is allowed to react chemically in the animal's metabolic system for a predetermined time after which the chemical reaction is terminated substantially instantly. The entire animal is then taken and analyzed to determine what if any N-nitroso compounds are present and the respective amounts of each. The animal could be one that has been raised under controlled laboratory conditions in order to prevent exposure of it to foreign substances which might interfere with the measurement of the present invention. In one set of experiments involving the present invention, the animals used were white mice, Swiss strain A. Substance introduced into their metabolic systems varied from common food to pure chemicals not commonly found in nature. Particular substances and their effects are discussed below.

In the preferred embodiments of the present invention the substances are introduced into the stomach of the test animal by gavage. This procedure places the substance completely within the animal's stomach at a precise and known point in time facilitating the second step of the invention.

After the substance is introduced, it is permitted to chemically react within the system of the test animal. If the time of substance introduction is known, the reaction time within the system may be measured. This information is significant in determining the rate of formation and absorption of various N-nitroso compounds, as discussed below. Also affecting the reaction time within the system is the means for termination of the chemical reaction. If the chemical reaction can be terminated substantially instantly and the substance was originally introduced at a known point in time, the total reaction time is easily measured. Precise timing is important as it has been discovered that N-nitroso compounds decay rapidly in the body. Thus, unless the introduction and the termination, discussed above, are substantially instantaneous, it will be difficult to obtain accurate results in relation to time.

Cryogenic techniques may be used for terminating chemical reactions instantly, as by immersing the animal in a very cold liquid causing the animal to freeze very quickly. Preferable are liquified gases, such as liquid nitrogen which has a temperature of approximately $-197°$ C. Liquified carbon dioxide gas may also be used and, in some instances, brine is usable. Some circumstances lend themselves to chemical freezing. In such cases sodium hydroxide or hydrochloric acid may be employed. Chemical freezing techniques may be particularly advantageous where specific organs, rather than an entire animal, are to be tested or where tissue or a very small animal such as a worm is to be tested.

Subsequent to freezing, the amount of N-nitroso compounds present in the animal is measured and the compounds may be identified. One means of measurement available entails the use of a Thermo Electron Analyzer Model No. 502 available from Thermo Electron Corporation of Waltham, Mass. This analyzer is usable in conjunction with a high pressure liquid chromatograph and/or a gas chromatograph. The operation of these systems is described in detail in the following U.S. patents:

U.S. Pat. Nos. 3,973,910, Method of Measuring the N-nitrosamine Content of a Sample by David H. Fine; 3,996,002 Method and Apparatus For Measuring the N-nitroso Compound Content of a Sample by David H. Fine; 3,996,009, Specific Compound Detection System by David H. Fine and David P. Lieb; 3,996,008, Specific Compound Detection System With Gas Chromatograph by David H. Fine, David P. Lieb and David P. Rounbehler; 3,996,003, Specific Compound Detection System With Liquid Chromatograph by David H. Fine and David Rounbehler; and 3,996,004, Detection System With Liquid Chromatograph by David H. Fine and David P. Rounbehler.

For the purpose of measuring the N-nitroso compounds present in the animal, it is necessary to reduce the animal to at least a liquid state. This is accomplished by reducing the frozen animal to a fine frozen powder and extracting the powder into a solvent which is compatible with the measurement system. One method for reducing the animal is placing the frozen animal along with some liquid nitrogen into an ordinary household blender. The blender is operated to produce a sufficiently fine powder for measurement purposes. The blender speed and the time of operation may be varied according to the requirements of the particular test.

For example, white mice (approximately 30 g, Swiss Strain A) were obtained from Charles River Breeding Laboratory, Massachusetts. Afer feeding by gavage, the mice were sacrificed by being immersed into liquid nitrogen. After ten seconds the frozen animal was removed from the liquid nitrogen and placed, whole, in a Waring blender together with additional liquid nitrogen. The complete animal, including fur, teeth, and bones, was blended to a fine frozen powder and transferred into a round-bottom flask containing 1 ml of 1N NaOH. Mineral oil was added to the flask and the contents analyzed for volatile N-nitroso compounds according to above described procedures.

The present invention may be used in various test circumstances. The simplest application would be a test of the absorption rate of various N-nitroso compounds by the body of the test animal. This may be accomplished by introducing the particular N-nitroso compound into the stomach of a plurality of test animals that are similar in type and weight and terminating the chemical reactions within these animals after different amounts of reaction time. For example, in one time dose study, mice were fed 50 ng of dimethylnitrosamine (DMN) is 50 microliters of saline solution and then sacrificed after varying periods of time. The amount of DMN recovered was seen to fall very rapidly in the first 1 to 15 minutes after gavage. In the first 1 or 2 minutes following feeding, more than half of the DMN was lost. After about 60 minutes the DMN reached a plateau of approximately 1.4 ng per mouse. Several animals would normally be tested without introduction of the compounds in order to determine zero reference levels for the compound.

Another application of the method of the present invention would be a measurement of the rate of formation of N-nitroso compounds from known precursors. For example, various substances such as amines, amides and amino acids are known to react with nitrite in a reaction known as nitrosation to form N-nitroso compounds. If precursors are introduced into a plurality of animals, with equal amounts of each precursor being given to each animal, and the reaction in each is allowed to continue for a different period of time before measurement, measurements of the N-nitroso compounds for all of the animals will show the timewise distribution of the effects of nitrosation and absorption in the animals. For example in one study mice were dosed by gavage, with 50 microliters of nitrite in a saline solution, and then with 50 microliters of an amine in a saline solution. Even when a mouse was frozen immediately after feeding, 23% of the amine was converted into DMN. After 5 minutes, 27% of the amine was in the form of DMN. After 60 minutes only 7% of the amine was in the form of DMN. Similarly, tests may be run using different amounts of precursors and nitrite to judge the effects of these various levels on nitrosation and absorption.

Tests using just precursors or just nitrites may be undertaken to determine the presence of either nitrites of precursors naturally within the body. In controlled experiments at zero time, mice were dosed by gavage with 50 microliters of a saline solution containing 1 microgram per milliliter of dimethylamine hydrochloride (a total dose of 50 ng). No trace of DMN could be detected. In a second set of controlled experiments at zero time, mice were dosed by gavage with 50 microliters of a saline solution containing 5 milligrams per milliliter of sodium nitrite (a total dose of 250 micrograms). This experiment yielded about 3.5 ng of DMN per mouse. This result implies that some DMN precursors are present naturally in the stomachs of the mice.

One important application of the method of the present invention is the examination of various types of food to determine their potential for creating N-nitroso compounds in vivo. Ever since the development of specific techniques for the measurement of N-nitroso compounds, knowledge of the amount of preformed N-nitroso compounds present in food samples has been available. However, no method has yet been devised which accurately measures the amount of N-nitroso compounds formed by various foods after introduction into the body. The method of the present invention allows much insight in this area. A wide variety of foodstuffs and their effects on various types of animals needs to be examined. The entire animal may be frozen and thereafter measured. However, to measure local effects, it is possible to sever various organs from the test animal and measure their N-nitroso compound content individually.

It is also possible to use the method of the present invention to test blood samples from various animals and from man after consumption of various types of foodstuffs. The procedure for testing blood samples is similar to that which has already been stated. First, the test animal is given food or a substance having N-nitroso compounds or N-nitroso compound precursors. The food or substance is allowed to react within the test subject and a blood sample is taken. Reactions within the blood are terminated instantly. For example, the blood is frozen in a cryogenic system and reduced to a powder by blending. The blood is then measured for the presence of N-nitroso compounds. Testing blood samples has the advantage that a single test animal can provide several blood samples at different times during the metabolic process.

The present invention may be used to determine the inhibiting effects of various substances on the nitrosation of precursors. For example, it is know tht ascorbic acid, under certain conditions, reacts with nitrite to prevent the nitrosation of precursors. With the method of the present invention, the effects of these inhibiting agents may also be tested in vivo.

It is possible to introduce substances into the biological system by means other than feeding (i.e. breathing or contacting). It is therefore contemplated that the method of this invention can measure N-nitroso compounds which accumulate in vivo from various environmental exposures.

As various changes could be made in the above method without departing from the scope of the invention, it should be understood that all matter contained in the above description shall be interpreted as illustrative and not in a limiting sense.

We claim:

1. A method for measuring in vivo N-nitroso compounds, comprising:
    introducing one or more substances selected from the group consisting of N-nitroso compounds and N-nitroso compound precursors directly into the system of a live test animal;
    permitting the substance to metabolically react within the animal;
    terminating metabolic reactions within said animal substantially instantly; and
    measuring the amount of N-nitroso compounds present in the entire animal.

2. The method of claim 1, wherein said terminating step comprises quickly freezing the entire animal.

3. The method of claim 2, wherein the freezing step comprises immersing said animal in a liquified gas.

4. A method for measuring in vivo N-nitroso compounds, comprising:
    introducing one or more substances selected from the group consisting of N-nitroso compounds and N-nitroso compound precursors directly into the system of a live test animal; permitting the substance to metabolically react within the animal;
    at the end of a predetermined period of metabolic reaction, terminating metabolic reactions within said animal substantially instantly by freezing;
    reducing the entire frozen animal to a fine frozen powder;
    dissolving the powder in a solvent; and
    measuring the amount of N-nitroso compounds in the powder and solvent.

5. The method of claim 1 wherein the substance is introduced into the digestive system of the animal.

6. The method of claim 1 wherein the substance is introduced into the stomach of a test animal by gavage.

7. The method of claim 1, wherein the substance consists of a nitrite plus a compound selected from the group consisting of amines, amides and amino acids.

8. A method for measuring in vivo N-nitroso compounds, comprising:
    introducing one or more substances selected from the group consisting of N-nitroso compounds and N-nitroso compound precursors directly into the system of a live test animal;
    permitting the substance to metabolically react within the animal;
    freezing the animal substantially instantly to instantly terminate metabolic reactions within the animal by immersing the animal in a liquidfied gas;
    reducing the entire frozen animal to a fine frozen powder;
    desolving said frozen powder in a solvent; and
    measuring the amount of N-nitroso compounds in the powder and solvent;

9. A method for measuring the N-nitroso compound content in the blood of a test animal comprising:
    introducing one or more substances selected from the group consisting of N-nitroso compounds and N-nitroso compound precursors into a biological system of the test animal;
    permitting the substance of metabolically react within the animal;
    taking a blood sample from the animal;
    terminating the metabolic reaction within the blood sample substantially instantly; and
    measuring the amount of N-nitroso compounds present in the blood sample.

10. A method for measuring the in vivo content of N-nitroso compounds in a viable animal, comprising:
    introducing one or more substances selected from the group consisting of N-nitroso compounds and N-nitroso compound precursors into the biological system of a viable animal;
    terminating metabolic reactions within at least a portion of said animal substantially instantly by freezing in a cryogenic system; and
    measuring the amount of N-nitroso compounds present in said portion.

11. A method for measuring the in vivo content of N-nitroso compounds in a viable animal comprising:
    introducing one or more substances selected from the group consisting of N-nitroso compounds and N-nitroso compound precursors into the biological system of a viable animal;
    thereafter terminating metabolic reactions within at least a portion of said animal substantially instantly by freezing such portion in a cryogenic system;
    reducing the frozen portion to a fine frozen powder;
    dissolving the powder in a solvent; and
    measuring the amount of N-nitroso compounds in the powder and solvent.

* * * * *